(12) United States Patent
Suzuki et al.

(10) Patent No.: US 6,727,088 B2
(45) Date of Patent: *Apr. 27, 2004

(54) PROCESS FOR PREPARATION OF (R)-1, 2-PROPANEDIOL BY MICROBES

(75) Inventors: Toshio Suzuki, Osaka (JP); Hideaki Idogaki, Osaka (JP); Atsushi Nakagawa, Osaka (JP); Miki Ueda, Asaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,619

(22) Filed: Dec. 20, 2001

(65) Prior Publication Data

US 2002/0132314 A1 Sep. 19, 2002

(30) Foreign Application Priority Data

Dec. 26, 2000 (JP) ........................................ 2000-394493

(51) Int. Cl.$^7$ ............................. C12N 1/20; C12P 41/00
(52) U.S. Cl. ..................................... 435/280; 435/253.3
(58) Field of Search ............................... 435/280, 253.3

(56) References Cited

U.S. PATENT DOCUMENTS 5,246,843 A  9/1993  Kasai et al. ................. 435/158

FOREIGN PATENT DOCUMENTS

| EP | 0 434 393 | 6/1991 |
|---|---|---|
| EP | 0 496 001 | 7/1992 |
| JP | 03-191795 | 8/1991 |
| JP | 06-030790 | 2/1994 |
| JP | 06-209781 | 8/1994 |
| JP | 07-147993 | 6/1995 |
| JP | 2001-149090 | 6/2001 |

OTHER PUBLICATIONS

XP 002197332—Abstract & Applied Microbiology and Biotechnology, vol. 40, No. 2–3, 1993, pp. 273–278.

Tetrahedron: Asymmetry vol. 5, No. 2. pp. 239–246 (1994) "A novel generation of optically active 1,2–diols from the racemates by using halohydrin dehydro–dechalogenase", Suzuki et al.

*Primary Examiner*—Sandra E. Saucier
(74) *Attorney, Agent, or Firm*—Wenderoth, Lind & Ponack, L.L.P.

(57) ABSTRACT

A process for preparation of (R)-1,2-propanediol which comprises cultivating a microorganism belonging to genus Pseudomonas or genus Alcaligenes which has ability to assimilate (S)-1,2-propanediol as a single carbon source, in a culture medium containing racemic 1,2-propanediol as a single carbon source and then isolating the remaining (R)-1,2-propanediol from the culture broth.

4 Claims, No Drawings

2

PROCESS FOR PREPARATION OF (R)-1, 2-PROPANEDIOL BY MICROBES

TECHNICAL FIELD

The present invention relates to a process for preparation of (R)-1,2-propanediol from racemic 1,2-propanediol, using a microorganism which has ability to assimilate (S)-1,2-propanediol as a single carbon source.

(R)-1,2-propanediol prepared by the present invention is very important and useful as an intermediate in preparing optically active compounds, such as pharmaceuticals, agrochemicals and physiologically active compounds.

PRIOR ART

In regard to a chemical method for preparation of an optically active 1,2-propanediol, a method by reduction of hydroxy acetone using BINAP catalyst by Kitamura et al. (Tetrahedron Lett., 32,4163–4166 (1991)) and a method by asymmetric hydrolysis using Co-Salen catalyst by Jacobsen et al. (Science, 277, 936–938 (1997) are known. But in order to prepare 1,2-propanediol with optically high purity by these methods, expensive chemical catalyst is necessary and therefore, these methods are hardly said to be an industrially economical method.

In regard to a biological method, a method for preparation of (R)-1,2-propanediol by asymmetric reduction of 1-hydroxy-2-propanone and 1-hydroxy-2-butanone using glycerol dehydrogenase is known (Journal of Organic Chemistry, 51, 25–36(1986)).

Further, a method of preparation for optically active 1,2-propanediol by stereoselectively oxidative degradation using resting cells of microorganisms belonging to a genus Pseudomonas strain by Nikaido et al. (Japanese patent publication A 6-30790). According to this method, as mentioned in the example thereof, after separately cultivating a large amount of microorganisms having ability to stereoselectively degrade 1,2-propanediol and changing thus obtained cells into resting cells, the cells must be subjected to the optical resolution.

The present inventors also reported a method of preparing optically active 1,2-diols and halogenohydrines using oxidative dehalogenation enzyme, namely halohydrin dehydro-dehalogenase derived from Alcaligenes sp. DS-S-7G (Tetrahedron: Asymmetry, 5, 239–246 (1994), Japanese patent publication A 7-147993).

However, in the above mentioned biological methods, co-enzyme such as NAD or NADP is necessary and the regeneration (recycling) of it becomes its reaction rate-limiting factor. These methods are not said to be an economical process for preparation of optically active 1,2-propanediol and therefore, the development of a more effective and practical method has been desired.

DETAILED DESCRIPTION OF INVENTION

The object of the present invention is to provide a more economical and technically simpler method of preparing (R)-1,2-propanediol from racemic 1,2-propanediol comparing with the known methods mentioned above.

The present inventors have searched microorganisms having ability to assimilate (S)-1,2-propanediol preferentially and further, to grow by assimilating (S)-1,2-propanediol as a single carbon source. As a result the present inventors have succeeded in isolating the objective microorganisms and have completed the present invention.

Namely, the present invention relates to a process for preparation of (R)-1,2-propanediol which is characterized in cultivating a microorganism belonging to genus Pseudomonas or genus Alcaligenes which has ability to assimilate (S)-1,2-propanediol as a single carbon source, in a culture medium containing racemic 1,2-propanediol as a single carbon source or a complete synthetic medium containing racemic 1,2-propanediol as a single carbon source, assimilating (S)-1,2-propanediol and then isolating the remaining (R)-1,2-propanediol from the culture broth.

The microorganisms used in the present invention (abbreviated as the present microorganisms), for example Pseudomonas sp. DS-SI-5, Pseudomonas nitroreducens DS-S-RP8 and Alcaligenes sp. DS-S-7G have also ability to assimilate (R)-3-halogeno-1,2-propanediol and in case of the assimilation thereof, hydrogen halide of the same amount as (R)-3-halogeno-1,2-propanediol which is assimilated is released (Japanese patent publication B 4-73999, Japanese patent publication A 2001-149090). Thus, the present microorganisms are strains showing stereoselective dehalogenation ability against halogenohydrin compounds.

Furthermore, although Pseudomonas sp. DS-SI-5 has not ability to assimilate 4-chloro-1,3-butanediol, this strain shows stereoselective dehalogenation activity against (S)-4-chloro-1,3-butandiol to produce (S)-hydroxy-γ-butyrolactone (Japanese patent publication A 2001-120296).

Furthermore, Pseudomonas sp. DS-SI-5 does not have ability to assimilate 1,3-propanediol, 3-amino-1,2-propanediol, 1,2-butanediol, 1,2-pentanediol and 1,2-hexanediol.

Moreover, the present inventors have found that the present microorganisms have ability to stereoselectively assimilate (S)-1,2-propanediol, can grow in the complete synthetic medium containing racemic 1,2-propanediol as a single carbon source and makes non-assimilated (R)-1,2-propanediol remain in the culture broth.

ENBODYMENT OF INVENTION

The present invention relates to a process for preparation of (R)-1,2-propanediol from racemic 1,2-propanediol, by preferentially assimilating (S)-1,2-propanediol, using a microorganism belonging to genus Pseudomonas or genus Alcaligenes which has ability to assimilate (S)-1,2-propanediol as a single carbon source, and by isolating remaining (R)-1,2-propanediol from the culture broth.

Illustratively, first the present microorganisms are cultivated in the complete synthetic medium containing racemic 1,2-propanediol or 3-chloro-1,2-propanediol as a single carbon source, inorganic nitrogen compounds such as various ammonium salts or nitrates as nitrogen source and a small amount of metal salt or phosphate, or in a usual nutrient medium containing organic carbon subsatances and nitrogen substances such as a bouillon medium or a peptone medium and inorganic nutrient sources to prepare seed microorganisms.

Then, a small amount of thus obtained culture broth or microorganism is inoculated with a medium containing racemic 1,2-propanediol as a single source (abbreviated as the medium used in the present invention) and the medium is cultivated to isolate remaining (R)-1,2-propanediol from the culture broth.

Namely, by preferentially assimilating (S)-1,2-propanediol from racemic 1,2-propanediol using the present microorganisms, non-assimilated (R)-1,2-propanediol is made remain in the culture broth and is isolated.

The cultivation is preferably carried out at optimum pH and at optimum temperature, for example at pH 4–10, preferably 5–9, at the temperature of 15–50° C., preferably 20–37° C. In case that pH value gradually decreases with progress of the assimilation, it is necessary to adjust pH in the solution to optimum pH by adding an alkaline substance. The solution is preferably controlled in optimum pH range by using a substance which can be usually used as an acid-neutralizing agent, such as an aqueous alkali carbonate solution such as a calcium carbonate solution, a sodium carbonate solution, a potassium carbonate solution, or an ammonium carbonate solution, an aqueous alkaline hydroxide solution such as a sodium hydroxide solution, a potassium hydroxide solution or a calcium hydroxide solution, or an aqueous ammonia solution.

The concentration of the substrate, namely racemic 1,2-propanediol as carbon source in the medium is preferably 1–15% (v/v), and the substrate may be added at once in the initial stage or in several times.

The cultivation is usually aerobically carried out under stirring or agitation, or under aerobical agitating-cultivation, and the cultivation time depends on the substrate-concentration and other cultural condition, but is preferably completed in 24–120 hours.

When the remaining amount of the substrate, namely racemic 1,2-propanediol becomes 50% comparing with the initial concentration of the substrate by gas chromatography etc., the cultivation is preferably quenched, or the end point may be preferably determined with the measurement of optical purity on the optically active compound in the medium. Namely, exactly when (S)-1,2-propanediol in the substrate, namely racemic 1,2-propanediol is completely assimilated, the cultivation is preferably quenched.

Thus obtained (R)-1,2-propanediol remaining in the culture broth is recovered and purified by the conventional method. For example, after removal of cells from the medium by centrifugation, the supernatant is condensed with an evaporator, extracted with a solvent such as ethyl acetate etc. The extract is dried over anhydrous magnesium sulfate, and then the solvent is evaporated in vacuo to obtain (R)-1,2-propanediol in syrup. The syrup may be further purified by distillation.

In case of the practice of the present invention, the present microorganisms, without previous cultivation thereof, may be directly inoculated with the medium used in the present invention, and the medium is cultivated in the same manner as mentioned above to recover or isolate (R)-1,2-propanediol from the culture broth.

According to the present optical resolution method, the medium used is hardly contaminated as it is the complete synthetic medium containing racemic 1,2-propanediol as a single carbon source and that as (S)-1,2-propanediol is assimilated by the present microorganism, it is extremely easy to isolate (recover) remaining (R)-1,2-propanediol from the culture broth.

The medium used for previous seed culture is not limited as long as the present microorganisms can grow in said medium.

For example, there are illustrated carbohydrates such as glucose or fluctose, alcohols such as racemic 3-chloro-1,2-propanediol, (R)-3-chloro-1,2-propanediol, racemic 3-bromo-1,2-propanediol, (R)-3-bromo-1,2-propanediol or racemic 1,2-propanediol, organic acids such as acetic acid, citric acid, malic acid, maleic acid, fumaric acid, or gluconic acid, or a salt thereof, or a mixture thereof, as carbon source.

For example, there are illustrated inorganic nitrogen compounds such as ammonium sulfate, ammonium nitrate, or ammonium phosphate, organic nitrogen compounds such as urea, peptone, casein, yeast extract, meat extract, corn steep liquor, or a mixture thereof, as nitrogen source.

Further, inorganic salts such as a phosphate, a magnesium salt, a potassium salt, a manganese salt, an iron salt, a zinc salt, a cooper salt, or if suitable, vitamins may be used.

As enzyme-inducing additives to prepare the microorganisms having high enzyme activity, to the above mentioned medium, a nutrient medium such as a peptone medium, or a bouillon medium may be added a racemic 3-halogeno-1,2-propanediol such as racemic 3-chloro-1,2-propanediol or racemic 3-bromo-1,2-propanediol, or racemic 1,2-propanediol.

The cultivation for preparing the seed culture can be carried out as in the usual manner, for example at pH 4–10, preferably 5–9, at the temperature of 15–50° C., preferably 20–37° C., and aerobically for 20–96 hours.

The present microorganisms are, as mentioned above, ones belonging to genus Pseudomonas and genus Alcaligenes which have ability to assimilate (S)-1,2-propanediol and can grow by assimilating (S)-1,2-propanediol as carbon source, and preferable ones are Pseudomonas sp. DS-SI-5, Pseudomonas nitroreducens DS-S-RP-8 and Alcaligenes sp. DS-S-7G.

These strains were identified as strains belonging to species or strains of genus Pseudomonas and genus Alcaligenes from their physiological and bacteriological properties and have been deposited with the International Patent Organism Depositary National Institute of Advanced Industrial Science and Technology, Japan under Budapest Treaty under following deposit numbers.

Deposit number of Pseudomonas sp. DS-SI-5: FERM BP-7080, which has been deposited at the National Institute of Bio-Science and Human-Technology, Agency of Industrial Science and Technology, of 1-3, Higashi 1-chome, Tsukuba-shi, Ibaraki-ken, 305-8566 Japan, on Oct. 7, 1999, under the Budapest Treaty; Deposit number of Pseudomonas nitroreducens DS-S-RP8: FERM BP-7793, which has been deposited at the International Patent Organism Depository, National Institute of Advanced Industrial Science and Technology of AIST Tsukuba Central 6, 1-1, Higashi 1-chome, Tsukuba-shi, Ibaraki-ken, 305-8566 Japan, on Jun. 29, 2001, under the Budapest Treaty; and Deposit number of Alcaligenes sp. DS-S-7G: FERM BP-3098, which has been deposited at the Fermentation Research Institute, Agency of Industrial Science and Technology, of 1-3, Higashi 1-chome, Tsukuba-shi, Ibaraki-ken, 305-8566 Japan, on Nov. 15, 1989, under the Budapest Treaty.

Pseudomonas nitroreducens DS-S-RP8 (FERM BP-7793) is new strains which is not described in the publication and its physiological and bacteriological properties are shown below.

| Growth in various media | |
|---|---|
| 1. Bouillon-agar plate medium (30° C., cultivation for 3 days) | |
| Speed of colony growth: | ordinary |
| Shape of colonies: | circular |
| Shape of colony surface: | smooth |
| Raised condition of colonies: | convex |
| Periphery of colonies: | entire |
| Contents of colonies: | homogeneous |
| Color of colonies: | pale yellow |
| Transparency of colonies: | translucent |

| Growth in various media | |
|---|---|
| *-continued* | |
| Gloss of colonies: | yes |
| Formation of soluble pigment: | none |
| 2. Bouillon-agar slant medium (30° C., cultivation for 3 days) | |
| Growth degree: | good |
| Growth condition: | stringy |
| shape of colony surface: | convex |
| shape of colony in section: | flat |
| Gloss of colonies: | yes |
| Color of colonies: | pale yellow |
| Transparency of colonies: | translucent |
| 3. Bouillon-liquid medium (30° C., cultivation for 3 days) | |
| Growth degree: | good |
| Generation of gas: | none |
| Coloring of medium: | none |
| Status | precipitation |
| 4. Bouillon-agar stuck medium (30° C., cultivation for 3 days) | |
| Growth place: | surface |
| Growth degree of surface: | good |
| 5. Bouillon-gelatin stuck medium | not liquefied |
| 6. Physiological properties | |
| Reduction on nitrate | + |
| V-P test | − |
| MR test | − |
| Production of indole | − |
| PPA | − |
| Production of H$_2$S | + |
| Decarboxylation of lysine | + |
| Utilization of citric acid | + |
| Utilization of inorganic nitrogen | |
| Ammnonium sulfate | + |
| Hydrolysis of starch | − |
| Catalase | + |
| Urease | − |
| Oxidase | + |
| Denitrification | + |
| Arginine dehydrase | + |
| β-Galactosidase | − |
| Hydrolysis of esuclin | − |
| Production of fluorescent pigment | |
| King's A | − |
| King's B | + |
| Litmus milk | |
| Agglutination | − |
| Reduction | − |
| Accumulation of PHB | + |
| O-F test | |
| D-Glucose | 0 |
| D-Galactose | 0 |
| D-Fructose | 0 |
| Glycerol | 0 |
| D-Mannitol | − |
| D-Gluconate | − |
| Utilization of carbon source | |
| D-Glucose | + |
| D-Galactose | − |
| D-Fructose | + |
| D-Mannnose | − |
| D-Maltose | − |
| Glycerol | − |
| D-Mannitol | − |
| D-Gluconate | + |
| 7. Morphological properties | |
| Shape of cells | rods |

| Growth in various media | |
|---|---|
| *-continued* | |
| Size of cells (μm) | 1.3–1.6 |
| Width of cells (μm) | 0.4–0.6 |
| Pleomorphisms of cell | none |
| Flagella | polar, single |
| Mobility | + |
| Gram stain | − |
| Spores | − |
| Acid fastness | − |
| Capsules | none |

The present invention is illustratively explained by following examples, but should not be limited by these examples. Percentage (%) in examples means % (w/v), if not defined otherwise.

EXAMPLE 1

| | |
|---|---|
| Ammonium sulfate | 1.0% |
| Disodium hydrogenphosphate.12H$_2$O | 0.02% |
| Dipotassium hydrogenphosphate | 0.02% |
| Sodium dihydrogenphosphate.2H$_2$O | 0.04% |
| Magnesium sulfate | 0.05% |
| Iron sulfate.7H$_2$O | 0.001% |
| Cooper sulfate.5H$_2$O | 0.0001% |
| Manganese nitrate.7H$_2$O | 0.0001% and |
| Calcium carbonate | 2.0% | was poured in an Erlenmeyer flask (500 ml) with a baffle and the medium was sterilized at 121° C. under the pressure for 15 minutes. Racemic 1,2-propanediol (1 ml) was added thereto to prepare a complete synthetic medium containing racemic 1,2-propanediol as a single carbon source.

Then, a loopful of cells of Pseudomonas sp. DS-SI-5 which was previously incubated on the slant agar medium (pH 7.2) containing polypeptone (1.0%), yeast extract (1.0%) and D-glucose (1.0%) was aseptically seeded to the above complete synthetic medium. The medium was cultivated with agitation (130 rpm) at 30° C. for 2 days.

The turbidity of the strain grown in the medium was 8.1 OD (at 660 nm). The remaining ratio of 1,2-propanediol at that time was 45% by the measurement with gas chromatography (column support: PEG20M, 60–80 mesh).

After the cultivation, the cells in the culture broth were taken out and removed by centrifugation to give a supernatant. The supernatant was condensed to 2 ml with an evaporator and extracted with ethyl acetate.

The extract was dried on anhydrous magnesium sulfate and the solvent was distilled in vacuo to give 1,2-propanediol (0.36 g) in syrup.

The measurement of optical purity of 1,2-propanediol thus obtained, after it was trifluoacetylated with trifluoroacetic acid anhydride, was carried out by subjecting to gas chromatography with capillary column: CHIRALDEX G-TA, astec in USA (inner diameter; 0.25 mm×30 m) (Suzuki et al., Tetrahedron: Asymmetry, Vol. 5, 239–246 (1994).

As a result, 1,2-propanediol recovered was more than 99% ee in the optical purity and was (R)-form.

Conditions on the above gas chromatography analysis were as follows:

Analysis temperature: Column temp. (60° C.), Inject temp.: 200° C., Carrier gas: nitrogen (flow 0.5 ml/min.), Split ratio: 200/1, Detection: FID 200° C.

Retention time of 1,2-propanediol derivatives: (R)-form, 11.4 min.; (S)-form, 17.6 min.

EXAMPLES 2 AND 3

In the same manner as above Example 1, by using Pseudomonas nitroreducens DS-S-RP8 or Alcaligenes sp. DS-S-7G instead of Pseudomonas sp. DS-SI-5, there were obtained the following results.

| Strain | Remaining Ratio | Optical purity |
| --- | --- | --- |
| (Ex.2) *Pseudomonas nitroreducens* DS-S-RP8 | 43% | >99% ee |
| (Ex.3) Alcaligenes sp. DS-S-7G | 30% | >98 ee |

EXAMPLE 4

The optical resolution was carried out in the complete synthetic medium in the same manner as above Example 1, except using 8 ml of racemic 1,2-propanediol which was added to the complete synthetic medium.

The turbidity of the strain grown in the medium after the cultivation for 5 days was 5.9 OD (at 660 nm). The remaining ratio of 1,2-propanediol at that time was 26% as a result of the measurement with gas chromatography (column support: PEG20M, 60–80 mesh).

After the cultivation, the culture broth was taken out, the cells were removed by centrifugation to give a supernatant. The supernatant was condensed to 2 ml with an evaporator and extracted with ethyl acetate. The extract was dried on anhydrous magnesium sulfate and the solvent was distilled in vacuo to give 1,2-propanediol (1.8 g) in syrup.

The measurement of 1,2-propanediol thus obtained was carried out in the same method as in Example 1. As a result the 1,2-propanediol was more than 99% ee in the optical purity and was (R)-form.

EXAMPLE 5

In the same manner as above Example 4, by using Pseudomonas nitroreducens DS-S-RP8 instead of Pseudomonas sp. DS-SI-5, there were obtained the following results.
Remaining Ratio: 35%, Optical purity: >99%ee

EXAMPLE 6

A nutrient medium (100 ml, pH 7.2) consisting of polypeptone (1.0%), yeast extract (1.0%) and D-glucose (1.0%) was poured in an Erlenmeyer flask (500 ml) with a baffle and sterilized at 121° C. under the pressure for 15 minutes to prepare an aqueous nutrient medium.

Then, a loopful of cells of Pseudomonas sp. DS-SI-5 which was previously incubated in a nutrient agar medium containing the above medium was seeded to the above aqueous nutrient medium. The culture medium was cultivated with agitation (130 rpm) at 30° C. for 24 hours.

The turbidity of the strain grown in the medium was 10.2 OD (at 660 nm). The cells were collected by centrifugation and were twice washed with phosphate buffer (50 mM, pH 7.2) to prepare washed cells. Then, the cells were suspended in the medium (100 ml) containing racemic 1,2-propanediol as a single carbon source shown in Example 1 and the medium was cultivated with agitation (130 rpm) at 30° C. for 2 days.

The ratio of remaining 1,2-propanediol in the solution was measured in the same manner as in Example 1 and the ratio was 42%. After the cultivation the cells were removed by centrifugation to give a supernatant. The recovery of 1,2-propanediol from the supernatant was carried out as the same as in Example 1 to give 0.35 g of 1,2-propanediol.

The measurement of each optical isomer of 1,2-propanediol thus obtained was carried out in the same manner as in Example 1. As a result, the 1,2-propanediol was more than 99% ee in the optical purity and was (R)-form.

EXAMPLES 7 AND 8

In the same manner as above Example 6, by using Pseudomonas nitroreducens DS-S-RP8 or Alcaligenes sp. DS-S-7G instead of Pseudomonas sp. DS-SI-5, there were obtained the following results.

| Strain | Remaining Ratio | Optical purity |
| --- | --- | --- |
| (Ex.7) *Pseudomonas nitroreducens* DS-S-RP8 | 41% | >99% ee |
| (Ex.8) Alcaligenes sp. DS-S-7G | 28% | >98 ee |

EXAMPLE 9

To a jar fermenter (Jar fermenter, prepared by Mitsuwa Rikagaku Co., Ltd.(5L), Model KMJ5B) was poured a medium (2.5L, pH 6.9) consisting of

| | |
| --- | --- |
| Ammonium sulfate | 1.0% |
| Disodium hydrogenphosphate.12$H_2O$ | 0.02% |
| Dipotassium hydrogenphosphate | 0.02% |
| Sodium dihydrogenphosphate.2$H_2O$ | 0.04% |
| Magnesium sulfate | 0.05% |
| Iron sulfate.7$H_2O$ | 0.001% |
| Cooper sulfate.5$H_2O$ | 0.0001% |
| Manganese nitrate.7$H_2O$ | 0.0001% | and the medium was sterilized at 121° C. under the pressure for 15 minutes. To the medium, racemic 1,2-propanediol (25 ml) was added to prepare the complete synthetic medium containing racemic 1,2-propanediol as a single carbon source.

Then, Pseudomonas sp. DS-SI-5 was previously cultivated with agitation in a nutrient medium (pH 7.2) containing polypeptone (1.0%), yeast extract (1.0%) and D-glucose (1.0%) at 30° C. for 24 hours and this culture broth (50 ml, 2% (v/v)) was inoculated with the above complete synthetic medium containing racemic 1,2-propanediol as a single carbon source. The medium was aerobically cultivated with agitation for 3 days under following conditions.
Temperature: 30° C., Aeration: 0.5L/min, Agitation: 500 rpm The measurement and control of pH was carried out with a connected pH controller and pH in the broth was adjusted to 6.9 with an aqueous 3N sodium hydroxide solution. The quantitative analysis and identification of the product was carried out in the same manner as in Example 1.

The turbidity of the strain grown in the medium after completion of the cultivation was 7.1 OD (at 660 nm) and at that time the ratio of remaining 1,2-propanediol was 40%. The grown cells were removed from the culture broth by centrifugation to give a supernatant. The recovery of 1,2-propanediol from the supernatant was carried out in the same method as in Example 1 to give 9.1 g of 1,2-propanediol.

The measurement of 1,2-propanediol thus obtained was carried out in the same method as in Example 1. As a result the 1,2-propanediol was more than 99% ee in the optical purity and was (R)-form.

EXAMPLES 10 AND 11

In the same manner as above Example 9, by using Pseudomonas nitroreducens DS-S-RP8 or Alcaligenes sp. DS-S-7G instead of Pseudomonas sp. DS-SI-5, there were obtained the following results.

| Strain | Remaining Ratio | Optical purity |
|---|---|---|
| (Ex. 10) *Pseudomonas nitroreducens* DS-S-RP8 | 38% | >99% ee |
| (Ex. 11) Alcaligenes sp. DS-S-7G | 31% | >98 ee |

EXAMPLE 12

The optical resolution was carried out in the complete synthetic medium in the same manner as above Example 9, except using 250 ml of racemic 1,2-propanediol which is added to the complete synthetic medium.

The turbidity of the strain grown in the medium after the cultivation for 5 days was 20.1 OD (at 660 nm) and at that time the ratio of remaining 1,2-propanediol was 35%. Then, the recovery of 1,2-propanediol from the culture broth was carried out in the same method as in Example 1 to give 70.1 g of 1,2-propanediol.

The measurement of 1,2-propanediol thus obtained was carried out in the same method as in Example 1. As a result the 1,2-propanediol was more than 99% ee in the optical purity and was (R)-form.

EXAMPLE 13

In the same manner as above Example 12, by using Pseudomonas nitroreducens DS-S-RP8 instead of Pseudomonas sp. DS-SI-5, there were obtained the following results.

Remaining Ratio: 36%, Optical purity: >99%ee

EFFECT OF PRESENT INVENTION

According to the present invention, by preferentially assimilating (S)-1,2-propanediol in racemic 1,2-propanediol using a microorganism belonging to genus Pseudomonas or genus Alcaligenes such as Pseudomonas sp. DS-SI-5, Pseudomonas nitroreducens DS-S-RP8 or Alcaligenes sp. DS-S-7G, there are obtainable (R)-1,2-propanediol industrially and economically.

What is claimed is:

1. A process for the preparation of (R)-1,2-propanediol, comprising: cultivating a microorganism Pseudomonas nitroreducens DS-S-RP8 (Deposit No.: FERM BP-7793) or Alcaligenes sp. DS-S-7G (Deposit No.: FERM BP-3098) which assimilates (S)-1,2-propanediol in a complete synthetic medium containing racemic 1,2-propanediol as a single carbon source, wherein the microorganism stereoselectively assimilates (S)-1,2-propanediol; and then isolating the remaining (R)-1,2-propanediol from the culture broth.

2. The process according to claim 1 wherein the microorganism is Pseudomonas nitroreducens DS-S-RP8 (Deposit No.: FERM BP-7793).

3. A process for the preparation of (R)-1,2-propanediol, comprising:

cultivating in a medium containing racemic 1,2-propanediol, a microorganism Pseudomonas nitroreducens DS-S-RP8 (Deposit No.: FERM BP-7793) or Alcaligenes sp. DS-S-7G (Deposit No.: FERM BP-3098), which microorganism stereoselectively assimilates (S)-1,2-propanediol in preference to (R)-1,2-propanediol, and then isolating (R)-1,2-propanediol from the culture broth.

4. Pseudomonas nitroreducens DS-S-RP8 (Deposit No.: FERM BP-7793).

* * * * *